US008586742B2

(12) United States Patent
Milstein et al.

(10) Patent No.: US 8,586,742 B2
(45) Date of Patent: Nov. 19, 2013

(54) PROCESS FOR PREPARING AMINES FROM ALCOHOLS AND AMMONIA

(75) Inventors: David Milstein, Rehovot (IL); Chidambaram Gunanathan, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 296 days.

(21) Appl. No.: 13/057,989

(22) PCT Filed: Aug. 10, 2009

(86) PCT No.: PCT/IL2009/000778
§ 371 (c)(1),
(2), (4) Date: Feb. 7, 2011

(87) PCT Pub. No.: WO2010/018570
PCT Pub. Date: Feb. 18, 2010

(65) Prior Publication Data
US 2011/0152525 A1    Jun. 23, 2011

Related U.S. Application Data

(60) Provisional application No. 61/087,708, filed on Aug. 10, 2008.

(51) Int. Cl.
C07F 15/00    (2006.01)
B01J 31/02    (2006.01)
(52) U.S. Cl.
USPC ............................................ 546/10; 502/167
(58) Field of Classification Search
USPC ............................................ 546/10; 502/167
See application file for complete search history.

(56) References Cited

U.S. PATENT DOCUMENTS

2009/0112005 A1    4/2009    Milstein

FOREIGN PATENT DOCUMENTS

WO    2007104357    9/2007
WO    2007104359    9/2007

OTHER PUBLICATIONS

Gunanathan, C. et al.: Selective synthesis of primary amines directly from alcohols and ammonia. Angewandte Chemie, vol. 47, pp. 8661-8664, 2008.*
Ahmad N, Levison JJ, Robinson SD, Uttlky MF, Wonchoba ER and Parshall GW (1974) Complexes of Ruthenium, Osmium, Rhodium, and Iridium Containing Hydride Carbonyl, or Nitrosyl Ligands. Inorganic Syntheses 15(45): 45-64.
Bartoli G et al., (2008) Efficient transformation of azides to primary amines using the mild and easily accessible CeCI3.7H2O/NaI system. J Org Chem 73(5): 1919-1924.
Chiron J and Galy JP (2003) Reactivity of the Acridine Ring: One-Pot Regioselective Single and Double Bromomethylation of Acridine and Some Derivatives. Synlett 2003(15): 2349-2350.
Constable DJC et al., (2007) Key Green Chemistry Research Areas—Perspective from Pharmaceutical Manufacturers. Green Chem. 9: 411-420.
Fabiano E, Golding BT and Sadeghi MM (1987) A simple conversion of alcohols into amines. Synthesis (2): 190-192.
Fujita K, Enoki Y and Yamaguchi R (2008) Cp*Ir-catalyzed N-alkylation of amines with alcohols. A versatile and atom economical method for the synthesis of amines. Tetrahedron 64(8): 1943-1954.
Gross T, Seayad AM, Ahmad M and Beller M (2002) Synthesis of primary amines: first homogeneously catalyzed reductive amination with ammonia. Org Lett 4(12): 2055-2058.
Gunanathan C, Ben-David Y and Milstein D (2007) Direct synthesis of amides from alcohols and amines with liberation of H2. Science 317(5839): 790-792.
Gunanathan C and Milstein D (2008) Selective synthesis of primary amines directly from alcohols and ammonia. Angew Chem Int Ed Engl 47(45): 8661-8664.
Gunanathan C, Shimon LJ and Milstein D (2009) Direct conversion of alcohols to acetals and H(2) catalyzed by an acridine-based ruthenium pincer complex. J Am Chem Soc 131(9): 3146-3147.
Hayes KS (2001) Industrial processes for manufacturing amines. Appl Catal A 221(1-2): 187-195.
Joó F (2002) Aqueous organometallic catalysis. Kluwer Academic Publishers, New York.
Kitamura M, Suga T, Chiba S and Narasaka K (2004) Synthesis of primary amines by the electrophilic amination of Grignard reagents with 1,3-dioxolan-2-one O-sulfonyloxime. Org Lett 6(24): 4619-4621.
Miriyala B, Bhattacharyya S and Williamson JS (2004) Chemoselective reductive alkylation of ammonia with carbonyl compounds: synthesis of primary and symmetrical secondary amine. Tetrahedron 60: 1463-1471.
Narayan S, Muldoon J, Finn MG, Fokin VV, Kolb HC and Sharpless KB (2005) "On water": unique reactivity of organic compounds in aqueous suspension. Angew Chem Int Ed Engl 44(21): 3275-3279.
Nùñez Magro AA, Eastham GR and Cole-Hamilton DJ (2007) The synthesis of amines by the homogeneous hydrogenation of secondary and primary amides. Chem Commun (Camb) (30): 3154-3156.
Reddy GVS, Rao GV, Subramanyam RVK and Iyengar DS (2000) A new novel and practical one Pot methodology for conversion of alcohols to amines. Syn Commun 30(12): 2233-2237.
Seayad A, Ahmed M, Klein H, Jackstell R, Gross T and Beller M (2002) Internal olefins to linear amines. Science 297 (5587): 1676-1678.
Sun W and Pelletier JC (2007) Efficient conversion of primary and secondary alcohols to primary amines. Tetrahedron Lett 48(44): 7745-7746.

(Continued)

Primary Examiner — Charanjit Aulakh
(74) Attorney, Agent, or Firm — Rodney J. Fuller; Booth Udall Fuller, PLC

(57) ABSTRACT

The present invention provides novel ruthenium based catalysts, and a process for preparing amines, by reacting a primary alcohol and ammonia in the presence of such catalysts, to generate the amine and water. According to the process of the invention, primary alcohols react directly with ammonia to produce primary amines and water in high yields and high turnover numbers. This reaction is catalyzed by novel ruthenium complexes, which are preferably composed of quinolinyl or acridinyl based pincer ligands.

17 Claims, No Drawings

(56) References Cited

OTHER PUBLICATIONS

Surry DS and Buchwald SL (2007) Selective Palladium-Catalyzed Arylation of Ammonia: Synthesis of Anilines as well as Symmetrical and Unsymmetrical Di- and Triarylamines. J Am Chem Soc 129: 10354-10355.

Van der Boom Me and Milstein D (2003) Cyclometalated phosphine-based pincer complexes: mechanistic insight in catalysis, coordination, and bond activation. Chem Rev 103(5): 1759-1792.

White EH and Elliger CA (1965) The conversion of alcohols into amines. J Am Chem Soc 87(22): 5261-5262.

Yamaguchi R, Kawagoe S, Asai C and Fujita K (2008) Selective synthesis of secondary and tertiary amines by cp*iridium-catalyzed multialkylation of ammonium salts with alcohols. Org Lett 10(2): 181-184.

Zhang J, Gandelman M, Shimon LJ and Milstein D (2007) Electron-rich, bulky PNN-type ruthenium complexes: synthesis, characterization and catalysis of alcohol dehydrogenation. Dalton Trans (1): 107-113.

Zhang J, Gandelman M, Shimon Ljw, Rozenberg H and Milstein D (2004) Electron-rich, bulky ruthenium PNP-type complexes. Acceptorless catalytic alcohol dehydrogenation. Organometallics 23(17): 4026-4033.

Zhang J, Leitus G, Ben-David Y and Milstein D (2005) Facile conversion of alcohols into esters and dihydrogen catalyzed by new ruthenium complexes. J Am Chem Soc 127(31): 10840-10841.

Zhang J, Leitus G, Ben-David Y and Milstein D (2006) Efficient homogeneous catalytic hydrogenation of esters to alcohols. Angew Chem Int Ed Engl 45(7): 1113-1115.

Zimmermann B, Herwig J and Beller M (1999) The First Efficient Hydroaminomethylation with Ammonia: With Dual Metal Catalysts and Two-Phase Catalysis to Primary Amines. Angew Chem Int Ed Engl 38(16): 2372-2375.

\* cited by examiner

PROCESS FOR PREPARING AMINES FROM ALCOHOLS AND AMMONIA

RELATED APPLICATION DATA

This application is the U.S. National Stage of PCT/IL2009/000778, filed Aug. 10, 2009, which claims priority to U.S. Provisional Patent Application No. 61/087,708, filed Aug. 10, 2008, the contents of each of which are herein incorporated by reference for all purposes.

FIELD OF THE INVENTION

The present invention relates to novel ruthenium catalysts, and to a process of preparing primary amines by reacting alcohols with ammonia in the presence of such catalysts.

BACKGROUND OF THE INVENTION

Amines are a very important family of compounds in chemistry and biology. They are widely used in the production of pharmaceuticals, fine chemicals, agrochemicals, polymers, dyestuffs, pigments, emulsifiers and plasticizing agents (1). Among the amines, the terminal primary amines (e.g. $RNH_2$ wherein R is an organic radical) are the most useful, but their selective synthesis is challenging, due to their high reactivity.

The conversion of alcohols to amines by conventional methods typically involves two to three steps, each step generally requiring isolation and purification, making the process cumbersome for even small-scale syntheses (2). Fewer classical methods are known for the stepwise, one-pot conversion of alcohols to primary amines, although such methods are not environmentally benign and are inappropriate for large scale production (3-6). Existing methods for the preparation of primary amines generally utilize stoichiometric amounts of toxic reagents and lead to poor selectivity and very low atom-economy (7-9). An attractive method for the preparation of secondary and tertiary linear amines by hydroaminomethylation of internal olefins was reported (10). Amines are also prepared by the reduction of amides, generally under harsh conditions to result in a mixture of products (11). Iridium and rhodium catalyzed preparation of amines from aldehydes was also reported (12). Although high hydrogen pressure is required for the reductive amination of aldehydes, and alcohols are formed as by-products, this method demonstrated the first homogeneous catalytic reductive amination process with ammonia. Lewis acid catalyzed reductive amination methods for the synthesis of amines are also known (13, 14). Recently, synthesis of arylamines was achieved by palladium-catalyzed arylation of ammonia in dioxane (15). Primary amines can be alkylated by alcohols to obtain secondary amines (16). Iridium-catalyzed multialkylation of ammonium salts with alcohols was reported for the synthesis of secondary and tertiary amines, but selective synthesis of primary amines remains as a tantalizing task (17).

Among the methods utilized for commercial production of amines (1, 18), by far, the largest and most utilized are based on the reaction of alcohols with ammonia. However, the solid acid catalyzed reaction of alcohols with ammonia requires very high temperatures (300-500° C.) and forms mixtures of primary, secondary and tertiary amines, and also large amounts of alkene as a result of dehydration. The metal-oxide catalyzed reaction of alcohols and amines at high temperature and pressure also results in mixtures of amines and has to be conducted under hydrogen pressure for catalyst stability. In addition, this reaction forms alkanes as a result of CO extrusion. (18)

Catalytic coupling of ammonia with organic substrates for the direct preparation of aryl and alkyl primary amines are considered to be two of the ten greatest challenges in catalysis (19). Atom economical methods to activate alcohols (replacing the Mitsunobu protocol) for the direct nucleophilic substitution and "N"-centered chemistry that precludes azides and hydrazine are among the most required processes in pharmaceutical industries (20). Selective catalytic synthesis of primary amines is a paradoxical challenge as the primary amines are more nucleophilic than ammonia and compete with it in reaction with electrophiles such as alkyl halides or aldehydes, producing secondary amines (21), which can also react, leading to the formation of mixtures of products.

Thus, selective, catalytic synthesis of primary amines directly from alcohols and ammonia with elimination of water, under relatively mild conditions, without producing waste, is highly desirable economically and environmentally. However, such a facile process is unknown.

Pincer complexes can have outstanding catalytic properties (22, 23). The applicants of the present invention previously reported the dehydrogenation of alcohols catalyzed by PNP— and PNN—Ru(II) hydride complexes (24). Whereas secondary alcohols lead to ketones (25, 26), primary alcohols are efficiently converted into esters and dihydrogen (25-26). A dearomatized PNN pincer complex was particularly efficient (28); it catalyzed this process in high yields under neutral conditions, in the absence of acceptors or promoters. US patent application publication no. US 2009/0112005, to the applicants of the present invention, describes methods for preparing amides, by reacting a primary amine and a primary alcohol in the presence of ruthenium catalysts, to generate the amide compound and molecular hydrogen.

Given the widespread importance of amines in biochemical and chemical systems, an efficient synthesis that avoids the shortcomings of prior art processes is highly desirable.

SUMMARY OF THE INVENTION

The present invention provides novel ruthenium based catalysts, and a process for preparing primary amines, by reacting a primary alcohol and ammonia in the presence of such catalysts, to generate the primary amine compound and water. As contemplated herein, the inventors have discovered a novel process for preparing amines in which primary amines are directly prepared from primary alcohols and ammonia under mild conditions, precluding the need for stoichiometric amounts of toxic reagents, high pressure, and harsh experimental conditions. The reaction is homogenously catalyzed by a novel, air stable ruthenium pincer complex, and can proceed in water, in various organic solvents, in the absence of a solvent, or in heterogeneous or homogeneous mixtures of water and an organic solvent. The simplicity, generality and excellent atom-economy of this process make it attractive for the transformations of alcohols to amines both in small and large scale applications.

The process of the invention, i.e., the direct catalytic conversion of alcohols and ammonia into amines and water is illustrated in Scheme 1. This novel, environmentally benign reaction can be used to produce various amines from very simple substrates, with high atom economy and without use of any stoichiometric activating agents, thus generating no waste.

Scheme 1:

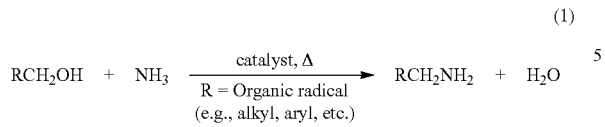

The applicants of the present invention have unexpectedly discovered that novel ruthenium complexes catalyze the reaction of primary alcohols with ammonia to form primary amines and $H_2O$. In one embodiment, the ruthenium catalyst is represented by the structure of formula A:

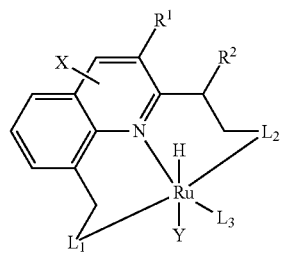

wherein

L$_1$ and L$_2$ are each independently selected from the group consisting of phosphine ($PR^aR^b$), amine ($NR^aR^b$), imine, sulfide (SR), thiol (SH), sulfoxide (S(=O)R), heteroaryl containing at least one heteroatom selected from nitrogen and sulfur; arsine ($AsR^aR^b$), stibine ($SbR^aR^b$) and an N-heterocyclic carbene represented by the structures:

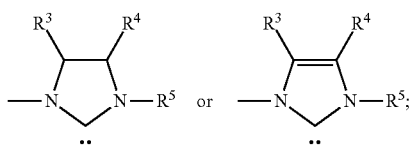

L$_3$ is a mono-dentate two-electron donor such as CO, $PR^aR^bR^c$, $NO^+$, $AsR^aR^bR^c$, $SbR^aR^bR^c$, $SR^aR^b$, nitrile (RCN), isonitrile (RNC), $N_2$, $PF_3$, CS, heteroaryl (e.g., pyridine, thiophene), tetrahydrothiophene and N-heterocyclic carbene;

$R^1$ and $R^2$ are either each hydrogen or together with the carbons to which they are attached represent a phenyl ring which is fused to the quinolinyl moiety of formula A so as to form an acridinyl moiety;

R, $R^a$, $R^b$, $R^c$, $R^3$, $R^4$ and $R^5$ are each independently alkyl, cycloalkyl, aryl, heterocyclyl, heteroaryl, alkylcycloalkyl, alkylaryl, alkylheterocyclyl or alkylheteroaryl;

Y is a monoanionic ligand such as halogen, OCOR, $OCOCF_3$, $OSO_2R$, $OSO_2CF_3$, CN, OH, OR, $NR_2$; a neutral solvent molecule $NH_3$, $NR_3$ or $R_2NSO_2R$, wherein R is as defined above. It is noted that when Y is neutral, the whole molecule carries a positive charge.

X represents one, two, three, four, five, six or seven substituents positioned at any carbon atom on the acridinyl moiety (in the case where $R^1$ and $R^2$ together with the carbons to which they are attached represent a phenyl ring which is fused to the quinolinyl moiety of formula A); or one, two, three, four or five substituents positioned on any carbon atom on the quinolinyl moiety (in the case where $R^1$ and $R^2$ are each hydrogen), and is selected from the group consisting of hydrogen, alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica) and a polymeric moiety (e.g., polystyrene).

In one embodiment, $R^1$ and $R^2$ are each H, and the ruthenium catalyst is represented by the structure:

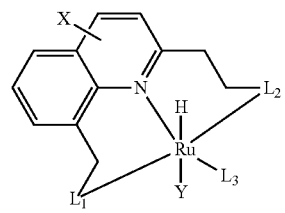

In another embodiment, $R^1$ and $R^2$ together with the carbon atoms to which they are attached form a phenyl ring which is fused to the quinolinyl moiety so as to form an acridinyl moiety, and the ruthenium catalyst is represented by the structure:

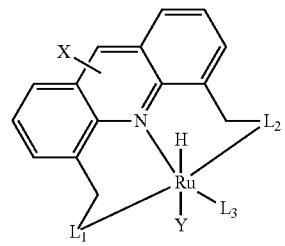

Several non-limiting embodiments of the ruthenium catalysts of the present invention are:

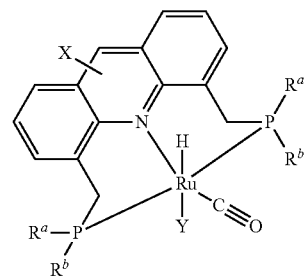

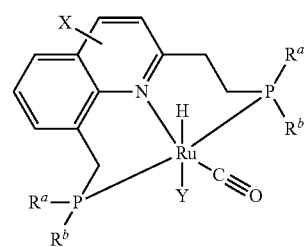

-continued

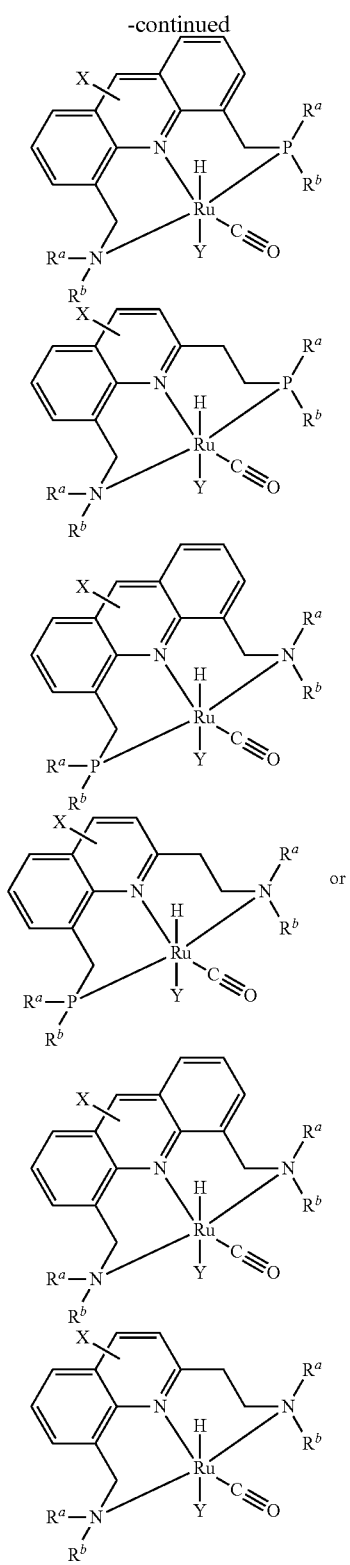

The substituents $R^a$ and $R^b$ are each independently alkyl, cycloalkyl, aryl, heterocyclyl, heteroaryl, alkylcycloalkyl, alkylaryl, alkylheterocyclyl or alkylheteroaryl. Some non-limiting examples are methyl, ethyl, isopropyl, t-butyl, cyclohexyl, cyclopentyl, phenyl, mesityl and the like.

The substituent Y is a monoanionic ligand such as halogen, OCOR, OCOCF$_3$, OSO$_2$R, OSO$_2$CF$_3$, CN, OH, OR or NR$_2$ wherein R is alkyl, cycloalkyl, aryl, heterocyclyl, heteroaryl, alkylcycloalkyl, alkylaryl, alkylheterocyclyl or alkylheteroaryl. Some non-limiting examples are F, Cl, Br, I, OCOCH$_3$, OCOCF$_3$, OSO$_2$CF$_3$ and other anionic ligands. A currently preferred Y ligand is a halogen, e.g., Cl. Y can also be a neutral solvent molecule, NH$_3$, NR$_3$, R$_2$NSO$_2$R and the like. When Y is neutral, the complex is charged, as exemplified below for embodiments wherein Y is a solvent ligand:

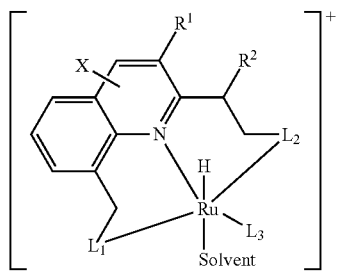

Examples of solvent ligand molecules (i.e., Y=solvent molecule) include, but are not limited to, acetone, dialkyl ketones (for examples 2-butanone), cyclic ketones (for example cyclohexanone), THF, anisole, dimethyl sulfoxide, acetonitrile, CH$_2$Cl$_2$, toluene, water, pyridine and the like.

In a currently preferred embodiment, L$_3$ is CO.

In a particular embodiment, the ruthenium catalyst is represented by the following structure of formula 1:

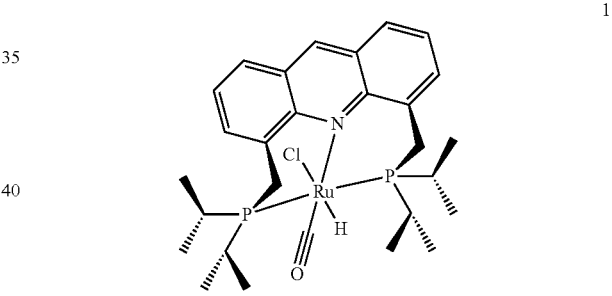

In an alternative embodiment, the ruthenium catalyst is a borane derivative of the catalyst of formula A, which is obtained by reacting complex A with sodium borohydride (NaBH$_4$). The borane derivative is represented by the structure of formula B.

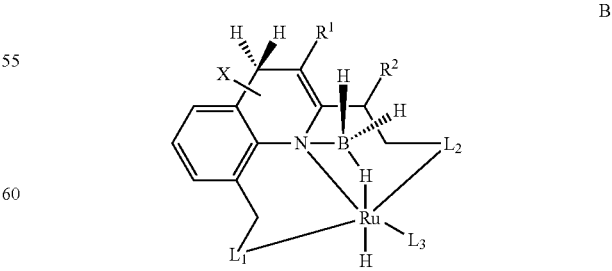

In one particular embodiment, the borane derivative is represented by the structure of formula 3. Complex 3 is sometimes designated herein as "RuH(BH$_3$)(A-$^i$Pr—PNP)(CO)".

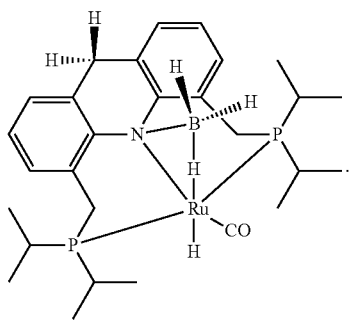

3

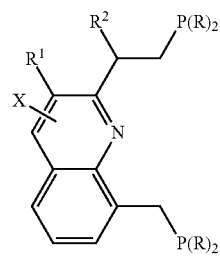

2A wherein each R is independently alkyl, cycloalkyl, aryl, heterocyclyl, heteroaryl, alkylcycloalkyl, alkylaryl, alkylheterocyclyl or alkylheteroaryl;

$R^1$ and $R^2$ are either each hydrogen, or together with the carbons to which they are attached represent a phenyl ring which is fused to the quinolinyl moiety so as to form an acridinyl moiety; and X represents one, two, three, four, five, six or seven substituents positioned at any carbon atom on the acridinyl moiety (in the case where $R^1$ and $R^2$ together with the carbons to which they are attached represent a phenyl ring which is fused to the quinolinyl moiety of formula A); or one, two, three, four or five substituents positioned on any carbon atom on the quinolinyl moiety (in the case where $R^1$ and $R^2$ are each hydrogen), and is selected from the group consisting of hydrogen, alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica) and a polymeric moiety (e.g., polystyrene).

The term "primary alcohol", as used herein, refers to a compound of the formula $RCH_2OH$ wherein R is an organic radical. A variety of primary alcohols can be used in the process of the invention. In one embodiment, the alcohol is represented by the formula $R^6CH_2OH$ wherein $R^6$ is selected from the group consisting of alkyl, cycloalkyl, aryl, heterocyclyl, heteroaryl, alkylcycloalkyl, alkylaryl, alkylheterocyclyl, alkylheteroaryl, and alkoxyalkyl. In several exemplary embodiments, the alcohol is selected from the group consisting of methanol, ethanol, 1-propanol, 1-butanol, 1-pentanol, 1-hexanol, benzyl alcohol, o-, m-, or p-methoxy benzyl alcohol, o-, m-, or p-halo benzyl alcohol, pyridine-2-yl-methanol, 2-furylmethanol, 2-phenylethanol, 2-methoxyethanol, 2-methyl-1-butanol, cyclohexylmethanol, and 3-methyloxetan-3-yl)methanol.

The term "ammonia", as used herein, refers to the compound "$NH_3$". Generally, ammonia is used as a gas. In an alternative embodiment, however, when water is used as the reaction solvent, the present invention contemplates the use of a solution of ammonium hydroxide ($NH_4^+OH^-$) in water. Thus, in accordance with this embodiment, the ammonia is provided as a solution of ammonium hydroxide in water.

The term "primary amine", as used herein, refers to a compound of the formula $RNH_2$ wherein R is an organic radical. The primary amine is generally a compound of formula $RNH_2$ wherein R is an organic radical. Preferably, the primary amine is a compound of formula $RCH_2NH_2$ wherein R is an organic radical. A variety of primary amines can be prepared in the process of the invention. In one embodiment, the primary amine obtained by the process of the invention is represented by the formula $R^6CH_2NH_2$ wherein $R^6$ is selected from the group consisting of alkyl, cycloalkyl, aryl, heterocyclyl, heteroaryl, alkylcycloalkyl, alkylaryl, alkylheterocyclyl, alkylheteroaryl, and alkoxyalkyl.

The methods of the present invention can be conducted in the absence or in the presence of a solvent. When a solvent is present, it can be aqueous (i.e., water), an organic solvent, or mixtures thereof. When mixtures of water and an organic solvent are used, the solvent system may form a homogenous solution or a heterogeneous mixture. Some non-limiting examples of organic solvents are benzene, toluene, o-, m- or p-xylene and mesitylene (1,3,5-trimethyl benzene), dioxane, THF, DME (dimethoxyethane), anisole, and cyclohexane.

The ammonia and primary alcohol can be used in equimolar amounts, however, it is preferred that ammonia is added in excess.

In another embodiment, the present invention provides precursors for preparing the ruthenium catalysts of the present invention. In one embodiment, the precursor is represented by the structure formula 2A:

One specific embodiment of formula 2A is a compound wherein each R is isopropyl, $R^1$ and $R^2$, together with the carbons to which they are attached represent a phenyl ring which is fused to the quinolinyl moiety so as to form an acridinyl moiety, and the compound has the structure of formula 2:

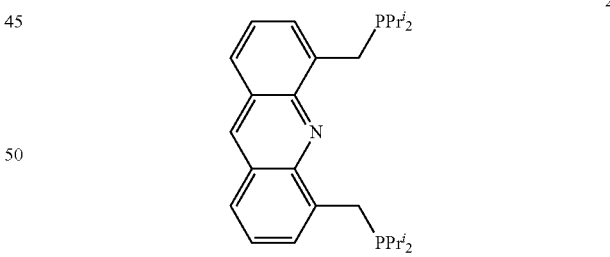

2

DETAILED DESCRIPTION OF THE PRESENT INVENTION

The present invention relates to novel ruthenium catalysts, and to a process for preparing primary amines, by reacting a primary alcohol and ammonia in the presence of such catalysts, to generate the amine and water as the only products.

This reaction is catalyzed by novel ruthenium complexes, which are preferably based on quinolinyl or acridinyl ligands, and no base or acid promoters are required.

In one embodiment, the ruthenium catalyst is represented by the following structure:

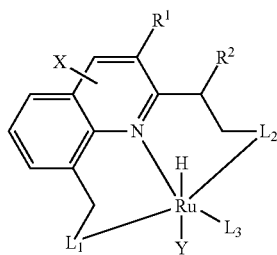

wherein

- $L_1$ and $L_2$ are each independently selected from the group consisting of phosphine ($PR^aR^b$), amine ($NR^aR^b$), imine, sulfide (SR), thiol (SH), sulfoxide (S(=O)R), heteroaryl containing at least one heteroatom selected from nitrogen and sulfur; arsine ($AsR^aR^b$), stibine ($SbR^aR^b$) and an N-heterocyclic carbene represented by the structure:

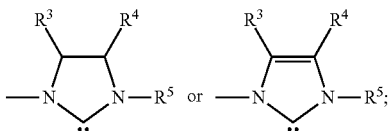

- $L_3$ is a mono-dentate two-electron donor such as CO, $PR^aR^bR^c$, $NO^+$, $AsR^aR^bR^c$, $SbR^aR^bR^c$, $SR^aR^b$, nitrile (RCN), isonitrile (RNC), $N_2$, $PF_3$, CS, heteroaryl (e.g., pyridine, thiophene) and tetrahydrothiophene;
- $R^1$ and $R^2$ are either each hydrogen or together with the carbons to which they are attached represent a phenyl ring which is fused to the quinolinyl moiety of formula A so as to form an acridinyl moiety;
- R, $R^a$, $R^b$, $R^c$, $R^3$, $R^4$ and $R^5$ are each independently alkyl, cycloalkyl, aryl, heterocyclyl, heteroaryl, alkylcycloalkyl, alkylaryl, alkylheterocyclyl or alkylheteroaryl;
- Y is a monoanionic ligand such as halogen, OCOR, $OCOCF_3$, $OSO_2R$, $OSO_2CF_3$, CN, OH, OR, $NR_2$; a neutral solvent molecule $NH_3$, $NR_3$ or $R_2NSO_2R$, wherein R is as defined above. It is noted that when Y is neutral, the whole molecule carries a positive charge.
- X represents one, two, three, four, five, six or seven substituents positioned at any carbon atom on the acridinyl moiety (in the case where $R^1$ and $R^2$ together with the carbons to which they are attached represent a phenyl ring which is fused to the quinolinyl moiety of formula A); or one, two, three, four or five substituents positioned on any carbon atom on the quinolinyl moiety (in the case where $R^1$ and $R^2$ are each hydrogen), and is selected from the group consisting of hydrogen, alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support (e.g., silica) and a polymeric moiety (e.g., polystyrene).

In one embodiment, $R^1$ and $R^2$ are each H, and the ruthenium catalyst is represented by the structure:

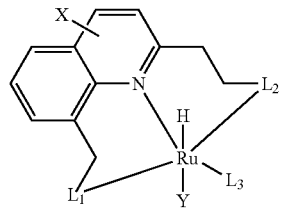

In another embodiment, $R^1$ and $R^2$ together with the carbon atoms to which they are attached form a phenyl ring which is fused to the quinolinyl moiety so as to form an acridinyl moiety, and the ruthenium catalyst is represented by the structure:

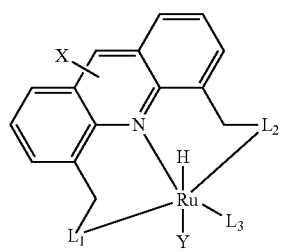

Several non-limiting embodiments of the ruthenium catalysts of the present invention are:

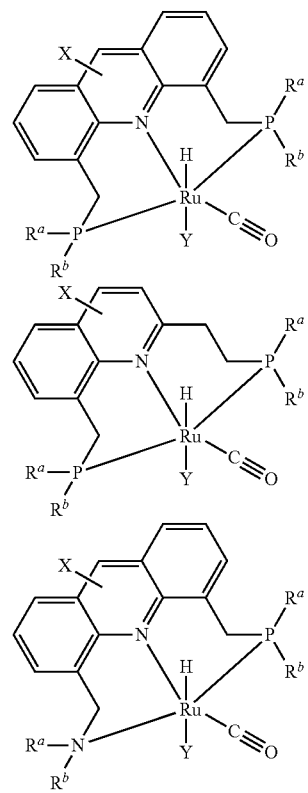

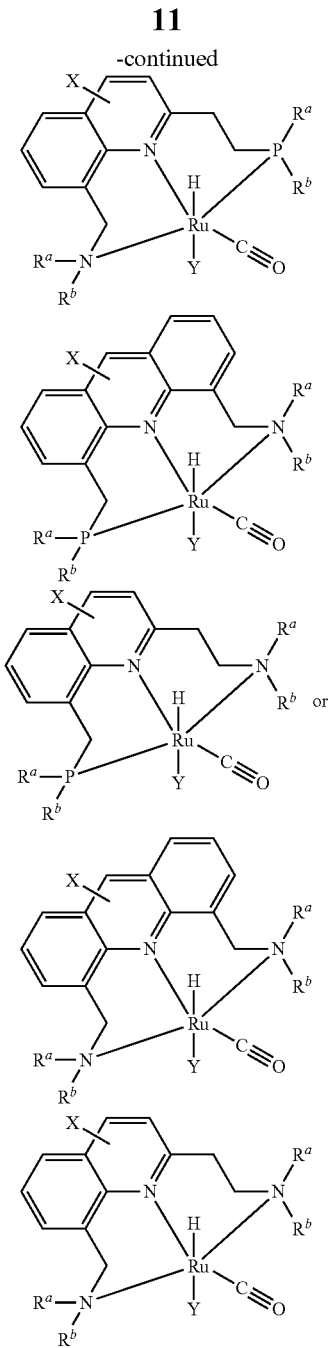

The substituents $R^a$ and $R^b$ are each independently alkyl, cycloalkyl, aryl, heterocyclyl, heteroaryl, alkylcycloalkyl, alkylaryl, alkylheterocyclyl or alkylheteroaryl. Some non-limiting examples are methyl, ethyl, isopropyl, t-butyl, cyclohexyl, cyclopentyl, phenyl, mesityl and the like.

The substituent Y is a monoanionic ligand such as halogen, $OCOR$, $OCOCF_3$, $OSO_2R$, $OSO_2CF_3$, $CN$, $OH$, $OR$ or $NR_2$ wherein R is alkyl, cycloalkyl, aryl, heterocyclyl, heteroaryl, alkylcycloalkyl, alkylaryl, alkylheterocyclyl or alkylheteroaryl. Some non-limiting examples are F, Cl, Br, I, $OCOCH_3$, $OCOCF_3$, $OSO_2CF_3$ and other anionic ligands. A currently preferred Y substituents is halogen, such as Cl. Y can also be a neutral solvent molecule, $NH_3$, $NR_3$, $R_2NSO_2R$ and the like. When Y is neutral, the complex is charged, as exemplified below for embodiments wherein Y is a solvent:

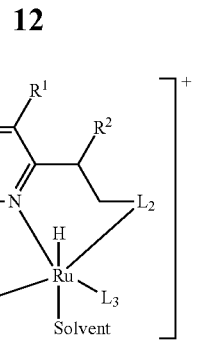

Examples of embodiments wherein Y is a solvent include, but are not limited to, acetone, dialkyl ketones (for examples 2-butanone), cyclic ketones (for example cyclohexanone), THF, anisole, dimethyl sulfoxide, acetonitrile, $CH_2Cl_2$, toluene, water, pyridine and the like.

In one currently preferred embodiment, $L_3$ is CO.

In a particular embodiment, the ruthenium catalyst is represented by the following structure of formula 1:

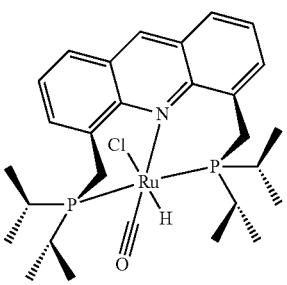

In one embodiment, the ruthenium catalyst is a borane derivative of the catalyst of formula A obtained by reacting compound A with sodium borohydride ($NaBH_4$), as illustrated in Scheme 2 below. The borane derivative is represented by the structure of formula B.

Scheme 2

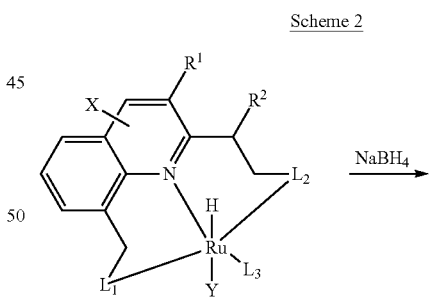

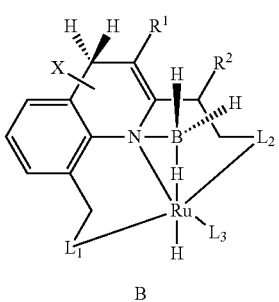

In one embodiment, the borane derivative is represented by the structure of formula 3:

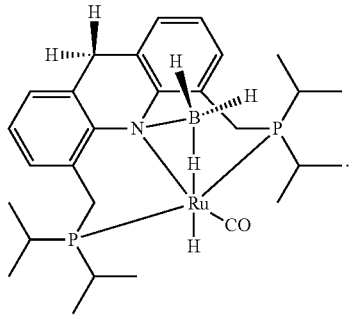

3

The borane derivative of formula 3 may be obtained by the process set forth in

Scheme 3:

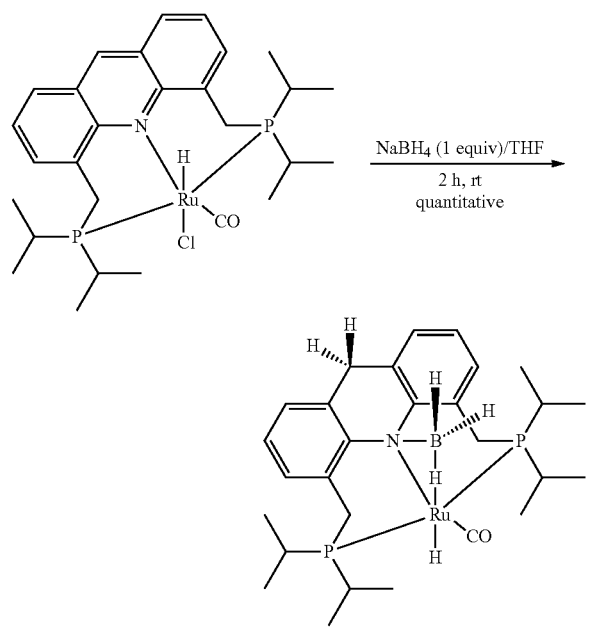

It is understood that when the catalyst includes one or more chiral centers, all stereoisomers are included in the scope of this invention.

A variety of primary alcohols can be used in the process of the invention. In one embodiment, the alcohol is represented by the formula $RCH_2OH$ wherein R is an organic radical. In another embodiment, the alcohol is represented by the formula $R^6CH_2OH$ wherein $R^6$ is selected from the group consisting of alkyl, cycloalkyl, aryl, heterocyclyl, heteroaryl, alkylcycloalkyl, alkylaryl, alkylheterocyclyl, alkylheteroaryl, aryloxyalkyl and alkoxyalkyl. In several exemplary embodiments, the alcohol is selected from the group consisting of methanol, ethanol, 1-propanol, 1-butanol, 1-pentanol, 1-hexanol, benzyl alcohol, o-, m-, or p-methoxy benzyl alcohol, o-, m-, or p-halo benzyl alcohol, (pyridine-2-yl)methanol, 2-furylmethanol, 2-phenylethanol, 2-methoxyethanol, 2-methyl-1-butanol, cyclohexylmethanol, and (3-methyloxetan-3-yl)methanol.

A variety of primary amines can be prepared in the process of the invention. In one embodiment, the primary amine obtained by the process of the invention is represented by the formula $RNH_2$ wherein R is an organic radical. In another embodiment, the primary amine obtained by the process of the invention is represented by the formula $RCH_2NH_2$ wherein R is an organic radical. Preferably, the primary amine obtained by the process of the invention is represented by the formula $R^6CH_2NH_2$ wherein $R^6$ is selected from the group consisting of alkyl, cycloalkyl, aryl, heterocyclyl, heteroaryl, alkylcycloalkyl, alkylaryl, alkylheterocyclyl, alkylheteroaryl, and alkoxyalkyl.

The methods of the present invention can be conducted in the absence or in the presence of a solvent. When a solvent is present, it can be aqueous (i.e., water), an organic solvent, or mixtures thereof. When mixtures of water and an organic solvent are used, the solvent system may form a homogenous solution or a heterogeneous mixture. Non-limiting examples of organic solvents are benzene, toluene, o-, m- or p-xylene mesitylene (1,3,5-trimethyl benzene), dioxane, THF, DME, anisole and cyclohexane. In one embodiment, when water is used as the reaction solvent the present invention contemplates the use of a solution of ammonium hydroxide ($NH_4^+$ $OH^-$) in water.

The stoichiometric ratios of ammonia to primary alcohol can vary, and depend on the particular alcohol and solvent used for the reaction. In one embodiment, the ammonia and alcohol can be added in equimolar amounts. In preferred embodiments, however, the ammonia is used in excess. Exemplary amounts of ammonia are between 1 atm to about 1000 atm, for example between 5 and 500 atm, 5 and 100 atm, 5 and 20 atm, preferably between 7 and 10 atm, for example 5, 5.5, 6, 6.5, 7, 7.5, 8, 8.5, 9, 9.5 or 10 atm. Exemplary corresponding amounts of alcohols are between 1 and 100 mmoles or higher amounts such as 100-500 mmoles, preferably between 1 and 10 mmoles, more preferably between 1 and 5 mmoles.

The reactions of the present invention can be performed for as long as needed so as to effect transformation of the primary alcohol to the primary amine, for example 1 hr to 24 hr or longer than 24 hr. The temperature range can vary from room temperature to heated conditions, for example up to 200° C.

In another embodiment, the process of the present invention can be used to prepare secondary amines by reaction of a primary amine and a primary alcohol. The primary alcohol can be any of the alcohols of the formula $R^6CH_2OH$ described above. The primary amine can be, for example, of the formula $R^7NH_2$ wherein $R^7$ is selected from the group consisting of alkyl, cycloalkyl, aryl, heterocyclyl, heteroaryl, alkylcycloalkyl, alkylaryl, alkylheterocyclyl, alkylheteroaryl, and alkoxyalkyl. In several exemplary embodiments, the primary amine is selected from the group consisting of methylamine, ethylamine, propylamine, butylamine, pentylamine, hexylamine, benzylamine, cyclohexylamine and the like. In accordance with this embodiment, the resulting secondary amine has the formula $R^6CH_2NR^7H$. Typically, the reaction between a primary alcohol and a primary amine to generate a secondary amine is conducted at elevated temperatures (e.g., 160-180° C.), in solvents such as xylene or mesitylene, for a period of time ranging from 24 to 72 hours. It is apparent to a person of skill in the art, however, that the reaction conditions can be optimized as deemed appropriate by a person with ordinary skill in the art.

Chemical Definitions

As used herein, the term alkyl, used alone or as part of another group, refers, in one embodiment, to a "$C_1$ to $C_{12}$ alkyl" and denotes linear and branched, saturated or unsaturated (e.g, alkenyl, alkynyl) groups, the latter only when the number of carbon atoms in the alkyl chain is greater than or equal to two, and can contain mixed structures. Preferred are alkyl groups containing from 1 to 6 carbon atoms ($C_1$ to $C_6$ alkyls). More preferred are alkyl groups containing from 1 to 4 carbon atoms ($C_1$ to $C_4$ alkyls). Examples of saturated alkyl groups include, but are not limited to, methyl, ethyl, n-propyl, isopropyl, n-butyl, iso-butyl, sec-butyl, tert-butyl, amyl, tert-amyl, and hexyl. Examples of alkenyl groups include, but are not limited to, vinyl, allyl, butenyl and the like. Examples of alkynyl groups include, but are not limited to, ethynyl, propynyl and the like. Similarly, the term "$C_1$ to $C_{12}$ alkylene" denotes a bivalent radical of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents. By way of illustration, an "alkoxyalkyl" is an alkyl that is substituted with an alkoxy group.

The term "cycloalkyl" used herein alone or as part of another group, refers to a "$C_3$ to $C_8$ cycloalkyl" and denotes any unsaturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups. An alkylcycloalkyl group denotes an alkyl group bonded to a cycloalkyl group.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubtituted or substituted through available carbon atoms with one or more groups defined hereinabove for alkyl. An alkylaryl group denotes an alkyl group bonded to an aryl group (e.g., benzyl).

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzo-heterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl, isoxazolyl and the like. The heteroaryl group can be unsubstituted or substituted through available atoms with one or more groups defined hereinabove for alkyl. An alkylheteroaryl group denotes an alkyl group bonded to a heteroaryl group.

The term "heterocyclic ring" or "heterocyclyl" used herein alone or as part of another group denotes a five-membered to eight-membered rings that have 1 to 4 heteroatoms, such as oxygen, sulfur and/or nitrogen. These five-membered to eight-membered rings can be saturated, fully unsaturated or partially unsaturated. Non-limiting examples of heterocyclic rings include piperidinyl, pyrrolidinyl, pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubtituted or substituted through available atoms with one or more groups defined hereinabove for alkyl. An alkylheterocyclyl group denotes an alkyl group bonded to a heterocyclyl group.

The term "alkoxy" refers to an alkyl bonded to an oxygen, e.g., methoxy, ethoxy, propoxy and the like. The term "aryloxy" refers to an aryl bonded to an oxygen, e.g., phenoxy, and the like. The term "halogen" refers to F, Cl, Br or I. The term "amide" refers to $RCONH_2$, RCONHR or $RCON(R)_2$ wherein R is as defined herein. The term "ester" refers to RCOOR wherein R is as defined herein. The term "cyano" refers to a CN group. The term "nitro" refers to a "$NO_2$" group.

The inorganic support which is attached to the pyridine ring in formula A can be, for example, silica, silica gel, glass, glass fibers, titania, zirconia, alumina and nickel oxide.

The polymer which is attached to the pyridine ring in formula A can be, for example, selected from polyolefins, polyamides, polyethylene terephthalate, polyvinylchloride, polyvinylidenechloride, polystyrene, polymethracrylate, natural rubber, polyisoprene, butadiene-styrene random copolymers, butadiene acrylonitrile copolymers, polycarbonate, polyacetal, polyphenylenesulfide, cyclo-olefin copolymers, styrene-acrylonitrile copolymers, ABS, styrene-maleic anhydride copolymers, chloroprene polymers, isobutylene copolymers, polystyrene, polyethylene, polypropylene, and the like.

The term "quinolinyl", as used herein, refers to a group represented by the structure:

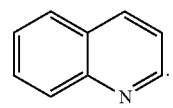

The term "acridinyl", as used herein, refers to a group represented by the structure:

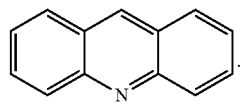

The quinolinyl or acridinyl functional groups can be attached to the Ruthenium catalysts of the present invention as readily understood by a person of skill in the art, and as described herein.

Exemplary Processes:

Benzyl alcohol was reacted with ammonia in the presence of ruthenium catalyst 1 (0.1 mol %) in refluxing mesitylene (b.p. 163° C.). As shown in Table 1 entries 1-3, 98% conversion of the alcohol was observed after 1 hr, yielding 69% of benzylamine and 28% of N-benzylidenebenzylamine. Slightly higher yields of benzylamine were observed at longer reaction times. Similar results were obtained at lower temperature in refluxing p-xylene (b.p. 138° C.) after 3 hrs (Table 1, entry 4). When the reaction was performed for the same period in toluene (b.p. 110.5° C.) the conversion of benzyl alcohol was less efficient (Table 1, entry 5), but after 13 h 99% conversion of benzyl alcohol occurred (Table 1, entry 6) to provide benzylamine in 87% yield along with N-benzylidenebenzylamine (12%). A further drop in reaction temperature using dioxane (b.p. 100° C.) as a solvent resulted in a lower conversion (Table 1, entry 7).

TABLE 1

Direct synthesis of benzylamine from benzyl and ammonia catalyzed by the ruthenium complex 1. Complex 1 (0.01 mmol), benzyl alcohol (10 mmol), ammonia (7.5 atm), and solvent (3 ml) were heated at reflux in a Fischer-Porter flask. Conversion of alcohols and yield of products were analyzed by Gas Chromatography (GC).

| Entry | Solvent[a] | Temp. (° C.)[b] | Time (hours) | Conversion of alcohol (%) | Yield (%) Benzylamine | N-Benzylidene-benzylamine |
|---|---|---|---|---|---|---|
| 1 | mesitylene | 180 | 10 | 100 | 73 | 24 |
| 2 | mesitylene | 180 | 2 | 98 | 71 | 25 |
| 3 | mesitylene | 180 | 1 | 98 | 69 | 28 |
| 4 | p-xylene | 160 | 3 | 100 | 73 | 26 |
| 5 | toluene | 135 | 3 | 30 | 18 | 11 |
| 6 | toluene | 135 | 13 | 99 | 87 | 12 |
| 7 | dioxane | 120 | 15 | 27 | 20 | 7 |

[a]Reactions were carried out in refluxing solvents.
[b]Temperature of oil bath.

To test whether increasing the concentration of ammonia relative to the alcohol might reduce the formation of imines (for example by capturing the contemplated intermediate aldehyde and preventing its reaction with the primary amine), complex 1 (0.01 mmol), benzyl alcohol (2.5 mmol) and ammonia (8 atm) in toluene were heated under reflux in a Fischer-Porter tube for 130 min, to get benzylamine (64.6%) and N-benzylidenebenzylamine (19.3%) whereas the conversion of benzyl alcohol was 84.7% (compare to entry 6, Table 1). Thus, increasing the concentration of ammonia did not affect the extent of formation of imine.

1-hexanol was chosen as a benchmark substrate for studying the direct amination reactions of simple aliphatic alcohols. 1-hexylamine and dihexylamine were formed, the yield of the latter increasing at higher reaction temperature and longer reaction time (Table 2). When the reaction was carried out in refluxing toluene for 15 h, 1-hexylamine was obtained in 63% yield whereas the major by-product was the corresponding imine (Table 2, entry 3). When the same reaction was prolonged to 24 h the yield of dihexylamine increased from 3 to 18% while the 1-hexylamine yield decreased to 58% (Table 2, entry 4).

TABLE 2

Direct synthesis of 1-hexylamine from 1-hexanol and ammonia catalyzed by the ruthenium complex 1. Complex 1 (0.01 mmol), 1-hexanol (10 mmol), ammonia (7.5 atm), and solvent (3 ml) were heated at reflux in a Fischer-Porter. Conversion of alcohols and yield of products were analyzed by GC.

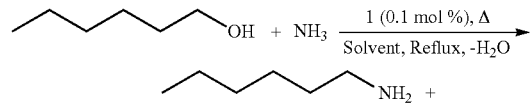

TABLE 2-continued

| Entry | Solvent | Time (hours) | Conversion of 1-hexanol (%) | Yield (%) 1-Hexylamine | Dihexylamine |
|---|---|---|---|---|---|
| 1 | mesitylene | 3 | 95 | 59 | 28.5 |
| 2 | mesitylene | 11 | 100 | 16.4 | 78.2 |
| 3* | toluene | 15 | 87.5 | 63 | 3 |
| 4† | toluene | 24 | 98.8 | 58 | 18 |

*Corresponding imine was the major by-product.
†Trihexylamine is formed as by-product.

The scope of the direct amination of alcohols with ammonia catalyzed by complex 1 (0.1 mol %) in refluxing toluene was studied with respect to the alcohol (Table 3). Aryl methanols underwent facile reaction to provide benzylamines in good yields. Benzyl alcohols with electron donating groups on the benzene ring reacted faster (Table 3, entries 1, 2) than benzyl alcohols with an electron withdrawing group (Table 3, entry 3). The electron rich heteroaryl methanols exhibited excellent selectivity for primary amines. Pyridine-2-yl-methanol and 2-furylmethanol were converted to the corresponding primary amines in 96 and 94.8% yields, respectively (Table 3, entries 4, 5). As with 1-hexanol, 1-pentanol also reacted to result in the formation of 1-pentylamine (61%) and dipentylamine (34.6%) (Table 3, entry 6). 2-Phenyletha-nol reacted similarly but the formation of secondary amines was less favored (Table 3, entry 7). 2-Methoxyethanol exhibited very good selectivity for the primary amine, providing 2-methoxyethylamine in 94.5% yield (Table 3, entry 8). Good selectivity was attained for the synthesis of aryl and heteroaryl methylamines. Increasing the steric hindrance at the β-position of alkyl alcohols diminished the formation of imines and the corresponding secondary amines and hence increased the selectivity and yields of primary amines (Table 3, entries 9-11). It is noteworthy that the strained 4-membered ring in the (3-methyloxetan-3-yl)methanol (Table 3, entry 9) remained intact, resulting in high yield of the primary amine. The reaction took place effectively also in neat alcohols, requiring no added solvent (Table 3, entries 6, 9).

Since the generation of a stoichiometric amount of water in the reaction didn't affect the catalysis by complex 1, the possibility of using water as a reaction medium was explored. Interestingly, the direct amination of alcohols with ammonia by complex 1 proceeded "on water" very well with excellent selectivity for primary amines. While water is the natural, greenest possible solvent, its current applications in catalysis

TABLE 3

Direct synthesis of amines from alcohols and ammonia catalyzed by the ruthenium complex 1. Complex 1 (0.01 mmol), alcohol (10 mmol), ammonia (7.5 atm), and toluene (3 ml) were heated in a Fischer-Porter. Conversion of alcohols and yield of products were analyzed by GC.

$$RCH_2OH + NH_3 \xrightarrow[\text{Toluene, Reflux, -H}_2\text{O}]{1 \text{ (0.1 mol \%)}, \Delta} RCH_2NH_2 + RCH=NCH_2R$$

| Entry | $RCH_2OH$ | Time (hours) | Conv. of alcohol | $RCH_2NH_2$ | Yield [†] (%) |
|---|---|---|---|---|---|
| 1 | 4-methylbenzyl alcohol | 12 | 100 | 4-methylbenzylamine | 83 |
| 2 | 4-methoxybenzyl alcohol | 14 | 100 | 4-methoxybenzylamine | 78 |
| 3 | 4-fluorobenzyl alcohol | 24 | 100 | 4-fluorobenzylamine | 91 |
| 4 | 2-pyridylmethanol | 30 | 100 | 2-pyridylmethylamine | 96 |
| 5 | furfuryl alcohol | 12 | 100 | furfurylamine | 94.8 |
| 6* | 1-pentanol | 20 | 97 | pentylamine | 61 (34.6)[‡] |
| 7 | 2-phenylethanol | 32 | 100 | 2-phenylethylamine | 68.8 |
| 8 | 2-methoxyethanol | 12 | 100 | 2-methoxyethylamine | 94.5 |
| 9* | 2-methyl-1-propanol | 18 | 93 | 2-methylpropylamine | 67.7 |
| 10 | cyclohexylmethanol | 25 | 95.5 | cyclohexylmethylamine | 82 |
| 11 | (3-methyloxetan-3-yl)methanol | 25 | 96.4 | (3-methyloxetan-3-yl)methylamine | 90 |

*Neat Reaction.
[†]The corresponding imine is the major byproduct in all reactions (analyzed by GC-MS and MS(ESI)); Its yield was not determined.
[‡]Yield of dipentylamine.

are limited (28). The presence of water in large excess was advantageous since it may have led to the hydrolysis of imines formed from further reactions of the primary amines, and thus enhanced the selectivity towards primary amines (Table 4, entry 1-3). The benzyl alcohols and 2-phenylethyl alcohol, which are insoluble in water at room temperature, formed a homogeneous solution on heating and thus the reaction might be considered "in water". Aliphatic alcohols such as 1-hexanol were not miscible with water even on heating and the reaction took place "on water" (29) (Table 4, entry 4). Surprisingly, when water soluble alcohols ([pyridin-2-yl]methanol and 2-methoxyethanol) were subjected to direct amination reaction "in water", the reaction became very sluggish even after prolonged heating (30 h) and the conversions were less efficient, in sharp contrast to excellent reactions in toluene (Table 3, entries 4 and 8).

Scheme 4:

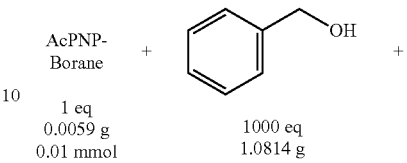

AcPNP-Borane + [benzyl alcohol] +

1 eq
0.0059 g
0.01 mmol 1000 eq
1.0814 g

TABLE 4

Direct synthesis of amines from alcohols and ammonia catalyzed by the ruthenium complex 1 in and on water. Complex 1 (0.01 mmol), alcohol (10 mmol), ammonia (7.5 atm), and water (3 ml) were heated at reflux in a Fischer-Porter. Conversion of alcohols and yield of products were analyzed by GC.

$$RCH_2OH + NH_3 \xrightarrow[\text{Water, 135°C.}]{1\ (0.1\ \text{mol}\ \%), \Delta} RCH_2NH_2 + RCH=NCH_2R$$

| Entry | RCH$_2$OH | Time (h) | Convn. | RCH$_2$NH$_2$ | Yield (%)† |
|---|---|---|---|---|---|
| 1 | benzyl alcohol | 18 | 100 | benzylamine | 95.4 |
| 2 | 4-methylbenzyl alcohol | 18 | 100 | 4-methylbenzylamine | 91.7 |
| 3 | 2-phenylethanol | 36 | 100 | 2-phenylethylamine | 80.4‡ |
| 4 | 1-hexanol | 24 | 92.4 | hexylamine | 54.8* |
| 5¶ | 1-hexanol | 28 | 89.4 | hexylamine | 74.3 |
| 6§ | 1-hexanol | 30 | 99 | hexylamine | 79.7 |
| 7§ | 1-pentanol | 30 | 98.7 | pentylamine | 70.0 |

†Corresponding imine was the major by-product in entries 1-3; Corresponding acid was the by product in entries 6-8.
‡Corresponding acids were found in aqueous layer.
*Hexamide was found in aqueous layer.
¶Mixture of 2 ml water and 2 ml toluene is used as solvent.
§Mixture of 1 ml water and 2 ml dioxane is used as solvent.

The inventors of the present application have further discovered that borane derivatives of the ruthenium catalysts of the present invention also act as catalysts in processes for converting primary alcohols to primary amines in accordance with the invention. Such borane derivatives are obtained by treatment of ruthenium catalysts with sodium borohydride (NaBH$_4$). For example, complex 3 (RuH(BH$_3$)(A-$^i$Pr—PNP)(CO)) can be used to covert benzyl alcohol to benzylamine in excellent yields, as illustrated in Scheme 4 below:

-continued

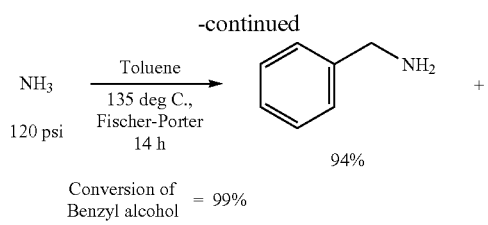

NH$_3$
120 psi

Toluene
135 deg C.,
Fischer-Porter
14 h

94%

Conversion of Benzyl alcohol = 99%

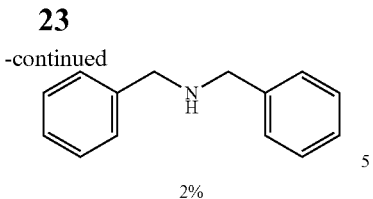

2%

It should be noted that instead of ammonia gas, a solution of ammonium hydroxide in water can be used. The reactions in water have several practical advantages as the aqueous and organic layers separate at the end of the reaction upon cooling and further purification of products could be carried out by vacuum distillation. The selectivity for the linear primary amines is improved by the use of co-solvents such as toluene or dioxane in water (Table 4, entries 5-7).

In addition to the selective synthesis of commercially important primary amines, the present invention also provides tools to install the amine functionality directly from alcohols in the synthesis of complex natural products and drugs without generating waste.

The disclosures of all cited references are incorporated by reference as if fully set forth herein.

EXPERIMENTAL DETAILS SECTION

Example 1

Preparation of Acridine-Based Pincer Complex RuHCl(A-$^i$Pr—PNP)(CO) 1

The novel, acridine-based pincer complex RuHCl(A-$^i$Pr—PNP)(CO) 1 was quantitatively prepared by reaction of the new electron-rich tridentate PNP ligand 2 with RuHCl(PPh$_3$)$_3$(CO) in toluene at 65° C. for 2 h (Scheme 5). $^{31}$P{$^1$H} NMR of 1 shows a singlet at 69.35 ppm. The $^1$H NMR spectrum of 1 exhibits a triplet resonance at −16.09 ppm for Ru—H. The "arm" methylene protons give rise to two double triplets at 3.50 and 5.24 ppm ($^2J_{HH}$=12.8 Hz, $^2J_{PH}$=3.7 Hz). One singlet resonance for C9H of the acridine ring appears at 8.15 ppm, representing an up field shift of 0.46 ppm relative to the corresponding proton of the ligand 2 (8.61 ppm), suggesting diminished aromaticity of acridine on complexation with ruthenium. The structure of complex 1 was determined by a single-crystal X-ray diffraction study, which reveals a distorted octahedral geometry around the ruthenium center (30). Upon complexation acridine looses its planarity and becomes bent at the middle aryl ring to adopt a boat shape with a dihedral angle of 167.6°. Convenient to practical applications, complex 1 is stable in air for several months.

Scheme 5. Synthesis of ligand 2 and complex 1.

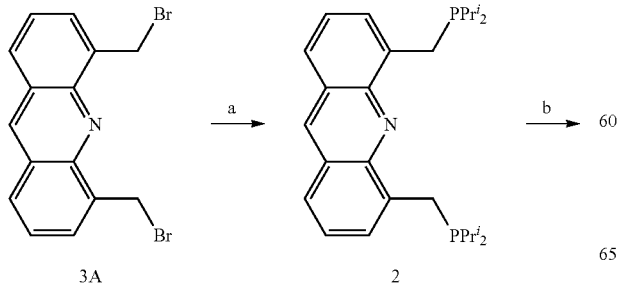

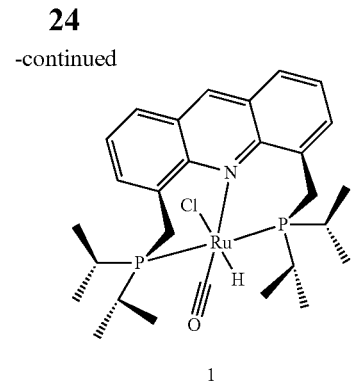

Key: a) i. Di-iso-propylphosphine/MeOH, 50° C., 48 h; ii. Triethylamine, r.t, 1 h, 83%. b) RuHCl(PPh$_3$)$_3$(CO)/toluene, 65° C., 2 h, quantitative or RuHCl(PPh$_3$)$_3$(CO)/THF, r.t, 9 h, 82%.

Example 2

Synthetic Methods

General Experimental

All experiments with metal complexes and phosphine ligands were carried out under an atmosphere of purified nitrogen in a Vacuum Atmospheres glovebox equipped with a MO 40-2 inert gas purifier or using standard Schlenk techniques. All solvents were reagent grade or better. All non-deuterated solvents were refluxed over sodium/benzophenone ketyl and distilled under argon atmosphere. Deuterated solvents were used as received. All solvents were degassed with argon and kept in the glove box over 4 Å molecular sieves. Most of the chemicals used in catalysis reactions were purified by vacuum distillation. However when commercial grade reagents were used comparable yield of products were obtained. Ultrapure water obtained from Barnstead NANOpure DIamond™ water purification system was used for catalysis reactions in water. 4,5-bis(bromomethyl)acridine (31) and RuHCl(CO)(PPh$_3$)$_3$ (32) were prepared according to literature procedures.

$^1$H, $^{13}$C and $^{31}$P NMR spectra were recorded at 500, 100, and 162 MHz, respectively, using a Bruker AMX-500 NMR spectrometers. $^1$H and $^{13}$C{$^1$H} NMR chemical shifts are reported in ppm downfield from tetramethylsilane. $^{31}$P NMR chemical shifts are reported in parts per million downfield from H$_3$PO$_4$ and referenced to an external 85% solution of phosphoric acid in D$_2$O. Abbreviations used in the NMR follow-up experiments: b, broad; s, singlet; d, doublet; t, triplet; q, quartet; m, multiplet, v, virtual.

4,5-Bis(bromomethyl)acridine (3A)$^{34}$: $^1$H NMR (CDCl$_3$): 5.31 (s, 4H, ArCH$_2$), 7.39 (dd, $^3J_{HH}$=8.5 Hz, $^4J_{HH}$=7.9 Hz, 2H, ArH), 7.82 (d, $^3J_{HH}$=6.7 Hz, 2H, ArH), 7.86 (d, $^3J_{HH}$=8.5 Hz, 2H, ArH), 8.65 (s, 1H, ArH).

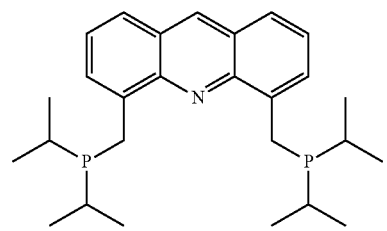 [SMILES: CC(C)P(Cc1cccc2cc3cccc(CP(C(C)C)C(C)C)c3nc12)C(C)C]

4,5-bis-(di-iso-propylphosphinomethyl)acridine (2): To an oven dried 100 mL Schlenk flask equipped with magnetic bar was added 4,5-bis(bromomethyl)acridine (3, 2 g, 5.48 mmol), diisopropyl phosphine (1.71 g, 14.52 mmol), and 25 mL MeOH. The flask was sealed and heated at 50° C. for 48 h with stirring. After cooling the reaction mixture, triethylamine (2.20 g, 21.78 mmol) was added and the reaction mixture was stirred at room temperature for 1 h. The solvents were removed under reduced pressure to obtain a yellow solid. The residue was washed with ether (4×15 mL) and the ether was removed under reduced pressure to yield a bright yellow solid. It was recrystallized from pentane/acetone mixture to yield 2.0 g (83%) of 4,5-bis[(diisopropylphosphanyl)methyl] acridine (2). $^{31}P\{^1H\}$NMR ($C_6D_6$): 12.35 (s). $^1$H NMR (CDCl$_3$): 1.03 (m, 24H, 2×P(CH(CH$_3$)$_2$)$_2$), 1.82 (m, 4H, (P—CH(CH$_3$)$_2$)$_2$), 3.72 (d, $^2J_{P,H}$=2.4 Hz, 4H, 2×P—CH$_2$), 7.39 (dd, $^3J_{HH}$=7.9 Hz, $^4J_{HH}$=6.7 Hz, 2H, ArH), 7.73 (d, $^3J_{HH}$=7.9 Hz, 2H, ArH), 7.81 (d, $^3J_{HH}$=6.7 Hz, 2H, ArH), 8.61 (s, 1H, ArH). $^{13}C\{^1H\}$NMR (CDCl$_3$): 19.45 (d, $^2J_{PC}$=11.5 Hz, P(CH(CH$_3$)$_2$)$_2$), 19.74 (d, $^2J_{PC}$=13.5 Hz, P(CH(CH$_3$)$_2$)$_2$), 23.32 (d, $^1J_{PC}$=18.1 Hz, 2×P—CH$_2$), 23.75 (d, $^1J_{PC}$=14.3 Hz, P(CH(CH$_3$)$_2$)$_2$), 125.38 (s, C$_1$, C$_8$, A-PNP), 125.58 (d, $^4J_{PC}$=2.0 Hz, C$_2$, C$_7$, A-PNP), 126.59 (s, C$_{8a}$, C$_{9a}$, A-PNP), 129.80 (d, $^3J_{PC}$=12.3 Hz, C$_3$, C$_6$, A-PNP), 136.32 (s, C$_9$, A-PNP), 139.44 (d, $^2J_{PC}$=7.5 Hz, C$_4$, C$_5$, A-PNP), 148.82 (d, $^3J_{PC}$=2.9 Hz, C$_{4a}$, C$_{10a}$, A-PNP). Assignment of signals was confirmed by DEPT 135.

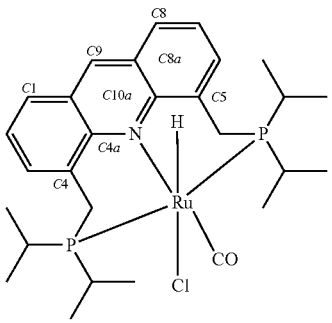

Synthesis of RuH(Cl)(A-$^i$Pr—PNP)(CO) 1: RuHCl(PPh$_3$)$_3$(CO) (301 mg, 0.32 mmol), ligand 2 (A-$^i$Pr—PNP; 153 mg, 0.35 mmol), and toluene (20 mL) were charged in a Schlenk flask sealed under the nitrogen atmosphere. The reaction mixture was heated at 65° C. for 2 hrs. The solvent was evaporated and the orange solid was washed with pentane and dried under vacuum overnight, resulting in pure complex 1 in a quantitative yield (191 mg). $^{31}P\{^1H\}$ NMR($C_6D_6$): 69.35 (s). $^1$H NMR ($C_6D_6$): −16.09 (vt, $^2J_{PH}$=19.2 Hz, 1H, Ru—H), 0.88 (q, $^3J_{PH}$=15.6 Hz, $^3J_{HH}$=7.3 Hz, 6H, P(CH(CH$_3$)$_2$)$_2$), 1.03 (q, $^3J_{PH}$=12.8 Hz, $^3J_{HH}$=6.4 Hz, 6H, P(CH(CH$_3$)$_2$)$_2$), 1.53 (overlapping m, 2H, P(CH(CH$_3$)$_2$)$_2$), 1.54 (q, $^3J_{PH}$=13.7 Hz, $^3J_{HH}$=7.3 Hz, 6H, P(CH(CH$_3$)$_2$)$_2$), 1.79 (q, $^3J_{PH}$=14.7 Hz, $^3J_{HH}$=7.3 Hz, 6H, P(CH(CH$_3$)$_2$)$_2$), 2.17 (m, 2H, P(CH(CH$_3$)$_2$)$_2$), 3.50 (dt, $^2J_{HH}$=12.8 Hz, $^2J_{PH}$=3.7 Hz, 2H, —CHHP), 5.24 (dt, $^2J_{HH}$=12.8 Hz, $^2J_{PH}$=3.7 Hz, 2H, —CHHP), 7.06 (t, $^3J_{HH}$=7.3 Hz, 2H, ArH), 7.33 (d, $^3J_{HH}$=7.3 Hz, 2H, ArH), 7.48 (d, $^3J_{HH}$=8.2 Hz, 2H, ArH), 8.15 (s, 1H, ArH). $^{13}C\{^1H\}$ NMR ($C_6D_6$): 18.60 (s, P(CH(CH$_3$)$_2$)$_2$), 19.42 (t, $^2J_{PC}$=2.9 Hz, P(CH(CH$_3$)$_2$)$_2$), 20.86 (s, P(CH(CH$_3$)$_2$)$_2$), 21.94 (s, P(CH(CH$_3$)$_2$)$_2$), 24.07 (t, $^1J_{PC}$=12.6 Hz, P(CH(CH$_3$)$_2$)$_2$), 25.83 (t, $^1J_{PC}$=10.3 Hz, P(CH(CH$_3$)$_2$)$_2$), 31.98 (t, $^1J_{PC}$=6.0 Hz, 2×CH$_2$P), 124.66 (s, C$_1$, C$_8$, A-PNP), 129.1 (s, C$_2$, C$_7$, A-PNP), 134.15 (d, $^2J_{PC}$=20.12 Hz, C$_4$, C$_5$, A-PNP), 135.03 (t, $^3J_{PC}$=3.4 Hz, C$_3$, C$_6$, A-PNP), 135.70 (s, C$_{8a}$, C$_{9a}$, A-PNP), 142.13 (s, C$_9$, A-PNP), 151.37 (t, $^3J_{PC}$=2.0 Hz, C$_{4a}$, C$_{10a}$, A-PNP), 203.40 (t, $^2J_{PC}$=11.4 Hz, Ru—CO). Assignment of signals was confirmed by DEPT 135. IR (KBr, pellet): 2048.7 ($v_{RuH}$), 1881.9 ($v_{CO}$) cm$^{-1}$, MS (ESI, MeOH): 569 (100%, (M-Cl)$^+$); MS (ESI, CH$_3$CN): 569 (42%, M-Cl)$^+$, 610 (100%, [(M-Cl)(CH$_3$CN)]$^+$).

Alternative method for the preparation of 1: To a suspension of RuHCl(PPh$_3$)$_3$(CO) (95.3 mg, 0.1 mmol) in THF (5 ml) was added ligand 2 (48 mg, 0.11 mmol), and the mixture was stirred at room temperature for 9 hrs. The orange solution was filtered and the filtrate was evaporated to dryness under vacuum. The orange residue was dissolved in minimum THF (0.5 mL) and slowly added to pentane (5 mL) to precipitate an orange solid, which was filtered and dried under vacuum (50 mg, 82%).

Synthesis of RuH(BH$_3$)(A-$^i$Pr—PNP)(CO)(Compound 3)

To a suspension of complex 1 (121 mg, 0.2 mmol) in THF (3 ml) was added a NaBH4 (0.21 mmol) in THF (2 ml) under nitrogen atmosphere. The mixture was stirred at room temperature for 2 hours. The colorless solution was filtered and the solvents evaporated. The complex was dried under vacuum overnight, resulting in AcPNP-Borane ruthenium complex (RuH(BH$_3$)(A-$^i$Pr—PNP)(CO) of formula 3) in quantitative yield (117 mg). This complex was fully characterized by NMR and by single-crystal X-ray crystallography. $^{31}P\{^1H\}$ NMR (Benzene-d$_6$): 51.57 (s). $^1$H NMR (Toluene-D$_8$, 291K): −9.27 (td, $^2J_{PH}$=22.0 Hz, $^2J_{HH}$=2.7 Hz, 1H, Ru—H), −5.40 (br s, 1H, BH$_3$), 0.78 (q, $^3J_{PH}$=11.0 Hz, $^3J_{HH}$=6.4 Hz, 6H, P(CH(CH$_3$)$_2$)$_2$), 1.22-1.32 (Overlapping 3 q, 18H, P(CH(CH$_3$)$_2$)$_2$), 1.51 (m, 2H, P(CH(CH$_3$)$_2$)$_2$), 2.04 (m, 2H, P(CH(CH$_3$)$_2$)$_2$), 2.35 (dt, $^2J_{HH}$=13.7 Hz, $^2J_{PH}$=2.7 Hz, 2H, —CHHP), 3.47 (d, $^2J_{HH}$=15.6 Hz, 1H, Ar—CHH—Ar), 3.63 (d, $^2J_{HH}$=13.7 Hz, 2H, —CHHP), 4.85 (d, $^2J_{HH}$=15.6 Hz, 1H, Ar—CHH—Ar), 6.53 (d, $^3J_{HH}$=7.3 Hz, 2H, ArH), 6.81 (t, $^3J_{HH}$=7.3 Hz, 2H, ArH), 7.01 (d, $^3J_{HH}$=7.3 Hz, 2H, ArH). $^{13}C\{^1H\}$ NMR ($C_6D_6$): 15.13 (t, $^2J_{PC}$=2.3 Hz, P(CH(CH$_3$)$_2$)$_2$), 19.80 (t, $^2J_{PC}$=2.0 Hz, P(CH(CH$_3$)$_2$)$_2$), 19.84 (s, P(CH(CH$_3$)$_2$)$_2$), 20.22 (s, P(CH(CH$_3$)$_2$)$_2$), 21.19 (t, $^1J_{PC}$=8.6 Hz, P(CH(CH$_3$)$_2$)$_2$), 26.75 (t, $^1J_{PC}$=14.3 Hz, P(CH(CH$_3$)$_2$)$_2$), 32.28 (t, $^1J_{PC}$=11.5 Hz, 2×CH$_2$P), 38.66 (s, C$_9$, ArCH$_2$Ar), 124.40 (s, C$_2$, C$_7$, A-PNP), 127.27 (s, C$_4$, C$_5$, A-PNP), 127.58 (s, C$_1$, C$_8$, A-PNP), 129.39 (t, $^3J_{PC}$=2.9 Hz, C$_3$, C$_6$, A-PNP), 141.12 (s, C$_{8a}$, C$_{9a}$, A-PNP), 152.18 (t, $^3J_{PC}$=3.4 Hz, C$_{4a}$, C$_{10a}$, A-PNP), 207.7 (t, $^2J_{PC}$=14.3 Hz, Ru—CO). IR (KBR pellets): 2413, 2357, 2333, 1913, 1462, 1437, 1036 cm$^{-1}$. Anal. Calcd. for C$_{28}$H$_{44}$BNOP$_2$Ru: C, 57.54; H, 7.59. Found: C57.49; H, 7.56.

General procedure for the catalytic direct amination of alcohols to amines: Complex 1 (0.01 mmol), alcohol (10 mmol), and a solvent (3 mL, if applicable) were added to a 90 mL Fischer-Porter tube under an atmosphere of purified nitrogen in a Vacuum Atmospheres glovebox. The tube was taken out of the box and ammonia (7.5 atm) was charged into the Fischer-Porter tube and the reaction mixture was refluxed in an oil bath covered by a protective shield for the specified time (Tables 1-3 in the reports). After cooling to room temperature, the products were analyzed by GC with toluene or mesitylene as an internal standard, using a HP-5 cross linked 5% PH ME Siloxane column (30 m×0.32 mm×0.25 μm film thickness) on a HP 6890 series GC system.

General procedure for the catalytic direct amination of alcohols to amines in water: Complex 1 (0.01 mmol), and alcohol (10 mmol) were taken in a 90 mL volume Fischer-Porter under an atmosphere of purified nitrogen in a Vacuum Atmospheres glovebox. The Fischer-Porter tube was taken out of glovebox and degassed water (3 ml) was added under an atmosphere of argon. Ammonia (7.5 atm) was charged into Fischer-Porter and the reaction mixture refluxed in an oil bath covered by a protective shield for the specified time (Table 4 in the reports). After cooling to room temperature, the products were analyzed by GC with mesitylene as an internal standard, using a HP-5 cross linked 5% PH ME Siloxane column (30 m×0.32 mm×0.25 μm film thickness) on a HP 6890 series GC system.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES AND NOTES

1. S. A. Lawrence, *Amines: Synthesis, Properties and Applications* (Cambridge University Press, 2005).
2. R. C. Larock, *Comprehensive Organic Transformations* (VCH, New York, ed. 2, 1999), pp. 753-879.
3. W. Sun, J. C. Pelletier, *Tetrahedron Lett.* 48, 7745 (2007).
4. E. Fabiano, B. T. Golding, M. M. Sadeghi, *Synthesis* 1987, 190 (1987).
5. G. V. S. Reddy, G. V. Rao, R. V. K. Subramanyam, D. S. Iyengar, *Syn. Commun.* 2000, 2233 (2000).
6. E. H. White, C. A. Eiliger, J. *J. Am. Chem. Soc.* 87, 5261 (1965).
7. G. Bartoli, G. D. Antonio, R. Giovannini, S. Giuli, S. Lanari, M. Paoletti, E. Marcantoni *J. Org. Chem.* 73, 1919 (2008) and references cited therein.
8. B. Miriyala, S. Bhattacharyyab, J. S. Williamson, *Tetrahedron* 60 1463 (2004).
9. M. Kitamura, T. Suga, S. Chiba, K. Narasaka, *Org. Lett.* 6, 4619 (2004).
10. A. Seayad, M. Ahmed, H. Klein, R. Jackstell, T. Gross, M. Beller, *Science* 297, 1676 (2002).
11. A. A. N. Magro, G. R. Easthamb D. J. Cole-Hamilton, *Chem. Commun.* 2007, 3154 (2007).
12. T. Gross, A. M. Seayad, M. Ahmad, M. Beller, *Org. Lett.* 4, 2055 (2002).
13. N. T. Christopher, W. V. Narayan, E. M. Mahmoud, World Pat. WO 2007/104357, (2007).
14. N. T. Christopher, W. V. Narayan, World Pat. WO 2007/104359, (2007).
15. D. S. Surry, S. L. Buchwald, *J. Am. Chem. Soc.* 129, 10354 (2007).
16. K. Fujita, Y. Enoki, R. Yamaguchi. *Tetrahedron* 64, 1943 (2008) and the references cited therein.
17. R. Yamaguchi, S. Kawagoe, C. Asai, K. Fujita, *Org. Lett.* 10, 181 (2008). The authors state in reference No. 15 of this letter, "We have not succeeded in selective synthesis of primary amines yet".
18. K. S. Hayes, *Appl. Catal. A* 221, 187 (2001).
19. J. Haggin, *Chem. Eng. News.* 71, 23 (1993).
20. D. J. C. Constable, P. J. Dunn, J. D. Hayler, G. R. Humphrey, J. L. Leazer, Jr., R. J. Linderman, K. Lorenz, J. Manley, B. A. Pearlman, A. Wells, A. Zaks, T. Y. Zhang, *Green Chem.* 9, 411 (2007).
21. B. Zimmermann, J. Herwig, M. Beller, *Angew. Chem. Int. Ed* 38, 2372 (1999).
22. M. E. van der Boom, D. Milstein, *Chem. Rev.* 103, 1759 (2003).
23. C. Gunanathan, Y. Ben-David, D. Milstein, *Science* 317, 790 (2007) and references cited therein.
24. J. Zhang, G. Leitus, Y. Ben-David, D. Milstein, *J. Am. Chem. Soc.* 127, 10840-10841 (2005).
25. J. Zhang, M. Gandelman, L. J. W. Shimon, D. Milstein, *Dalton. Trans.* 2007, 107-113 (2007).
26. J. Zhang, M. Gandelman, L. J. W. Shimon, D. Milstein, *Organometallics* 23, 4026-4033 (2004).
27. J. Zhang, G. Leitus, Y. Ben-David, D. Milstein, *Angew. Chem. Int. Ed.* 45, 1113-1115 (2006).
28. F. Joó, *Aqueous Organometallic Catalysis* (Kluwer Academic Publishers 2002).
29. S, Narayan, J. Muldoon, M. G. Finn, V. V. Fokin, H. C. Kolb, K. B. Sharpless. *Angew. Chem. Int. Ed* 44, 3275 (2005).
30. Structural data of complex 1 will be disclosed in due course.
31. Chiron, J. Galy, J, -P. synlett. 2003, 2349 (2003).
32. Ahmad, N.; Levison, J. J.; Robinson, S. D.; Uttley, M. F. *Inorg. Synth.* 15, 45 (1974).

What is claimed is:
1. A ruthenium catalyst represented by the structure of formula A:

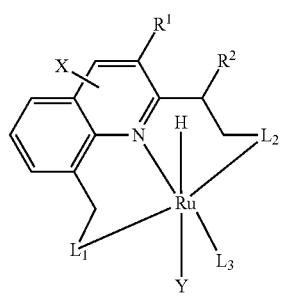

wherein
L$_1$ and L$_2$ are each independently selected from the group consisting of phosphine (PR$^a$R$^b$), amine (NR$^a$R$^b$), imine, sulfide (SR), thiol (SH), sulfoxide (S(=O)R), heteroaryl containing at least one heteroatom selected from nitrogen and sulfur; arsine (AsR$^a$R$^b$), stibine (SbR$^a$R$^b$) and a N-heterocyclic carbene represented by the structures:

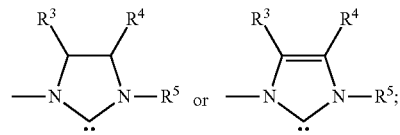

L$_3$ is a mono-dentate two-electron donor selected from the group consisting of CO, PR$^a$R$^b$R$^c$, NO$^+$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl and tetrahydrothiophene;

R$^1$ and R$^2$ are either each hydrogen or together with the carbons to which they are attached represent a phenyl ring which is fused to the quinolinyl moiety so as to form an acridinyl moiety;

R, R$^a$, R$^b$, R$^c$, R$^3$, R$^4$ and R$^5$ are each independently alkyl, cycloalkyl, aryl, heterocyclyl, heteroaryl, alkylcycloalkyl, alkylaryl, alkylheterocyclyl or alkylheteroaryl;

Y is halogen, OCOR, OCOCF$_3$, OSO$_2$R, OSO$_2$CF$_3$, CN, OH, OR, NR$_2$, NH$_3$, NR$_3$, R$_2$NSO$_2$R, or a neutral solvent molecule, wherein R is as defined above; and X represents one, two, three, four, five, six or seven substituents positioned at any carbon atom on the acridinyl moiety; or one, two, three, four or five substituents positioned on any carbon atom on the quinolinyl moiety, and is selected from the group consisting of hydrogen, alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety.

2. The ruthenium catalyst according to claim 1, wherein R$^1$ and R$^2$ are each H, and the ruthenium catalyst is represented by the structure:

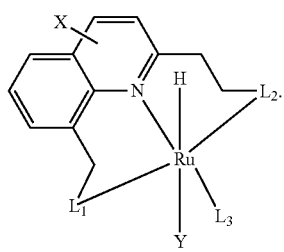

3. The ruthenium catalyst according to claim 1, wherein R$^1$ and R$^2$ together with the carbon atoms to which they are attached form a phenyl ring, and the ruthenium catalyst is represented by the structure:

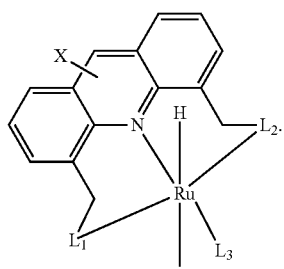

4. The ruthenium catalyst according to claim 1, which is represented by any of the following structures:

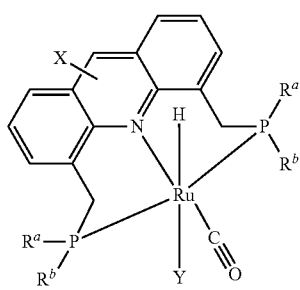

-continued

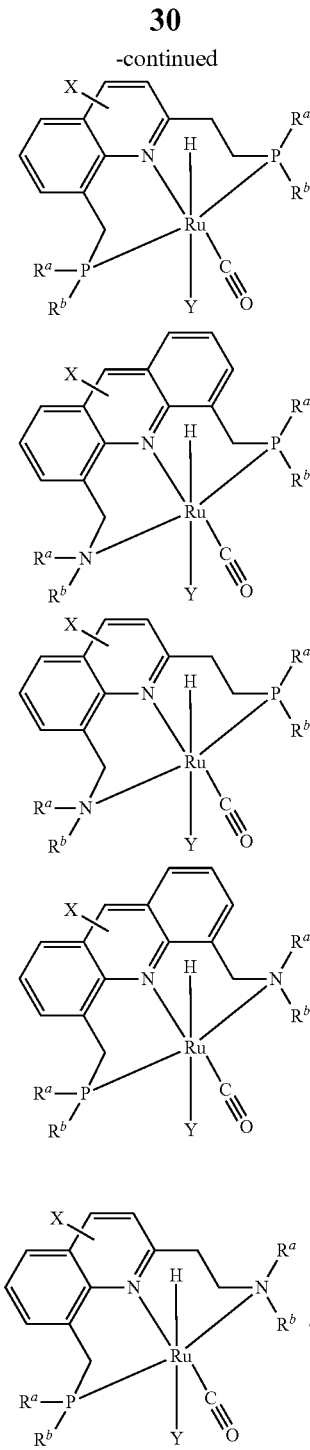

or

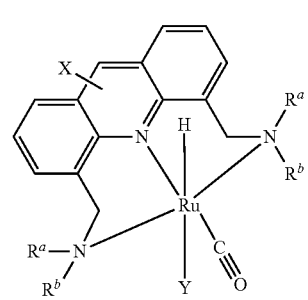

-continued

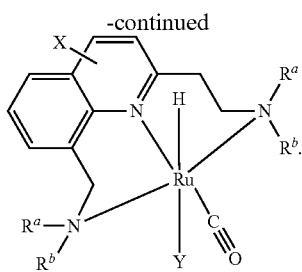

5. The ruthenium catalyst according to claim 1, which is represented by the structure of formula 1:

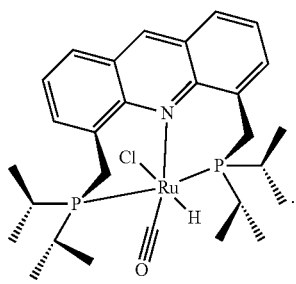

6. The ruthenium catalyst according to claim 1, wherein Y is halogen.

7. The ruthenium catalyst according to claim 1, wherein $L_3$ is CO.

8. A process for preparing a primary amine, comprising the step of reacting a primary alcohol and ammonia in the presence of the ruthenium catalyst according to claim 1, thereby generating the primary amine.

9. The process according to claim 8, wherein the primary alcohol is represented by the formula $R^6CH_2OH$ wherein $R^6$ is selected from the group consisting of alkyl, cycloalkyl, aryl, heterocyclyl, heteroaryl, alkylcycloalkyl, alkylaryl, alkylheterocyclyl, alkylheteroaryl and alkoxyalkyl.

10. The process according to claim 8, wherein the alcohol is selected from the group consisting of methanol, ethanol, 1-propanol, 1-butanol, 1-pentanol, 1-hexanol, benzyl alcohol, o-, m-, or p-methoxy benzyl alcohol, o-, m-, or p-halo benzyl alcohol, pyridine-2-yl-methanol, 2-furylmethanol, 2-phenylethanol, 2-methoxyethanol, 2-methyl-1-butanol, cyclohexylmethanol and (3-methyloxetan-3-yl)methanol.

11. The process according to claim 8, wherein the reaction is conducted in the presence of a solvent, wherein the solvent is water or an organic solvent selected from the group consisting of benzene, toluene, o-, m- or p-xylene mesitylene (1,3,5-trimethyl benzene, dioxane, THF, DME, anisole and cyclohexane.

12. The process according to claim 11, wherein the solvent is water, and the ammonia is provided as a solution of ammonium hydroxide in water.

13. The process according to claim 11, wherein the solvent is a mixture of water and an organic solvent, wherein the water and organic solvent form a homogenous solution, or wherein the water and organic solvent form a heterogeneous mixture.

14. The process according to claim 8, wherein the reaction is conducted in the absence of a solvent.

15. The process according to claim 8, wherein excess ammonia is used.

16. A process for preparing a ruthenium catalyst of formula A according to claim 1 wherein $L_1$ and $L_2$ are each phosphine ($PR^aR^b$), comprising the step of converting a precursor of formula 2A to said compound of formula A

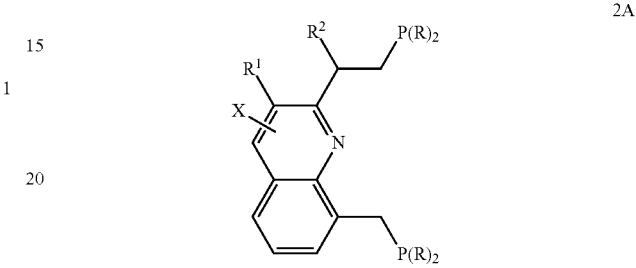

wherein
each R is independently alkyl, cycloalkyl, aryl, heterocyclyl, heteroaryl, alkylcycloalkyl, alkylaryl, alkylheterocyclyl or alkylheteroaryl;
$R^1$ and $R^2$ are either each hydrogen, or together with the carbons to which they are attached represent a phenyl ring which is fused to the quinolinyl moiety so as to form an acridinyl moiety; and
X represents one, two, three, four, five, six or seven substituents positioned at any carbon atom on the acridinyl moiety; or one, two, three, four or five substituents positioned on any carbon atom on the quinolinyl moiety, and is selected from the group consisting of hydrogen, alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety.

17. The process according to claim 16, wherein the compound of formula 2A is represented by the structure of formula 2:

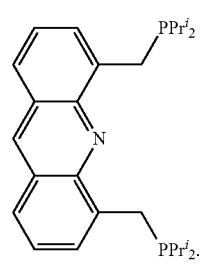

* * * * *